United States Patent [19]

Hanson et al.

[11] Patent Number: 5,523,219
[45] Date of Patent: Jun. 4, 1996

[54] ENZYMATIC HYDROLYSIS METHOD FOR THE PREPARATION OF C-10 HYDROXYL-BEARING TAXANES AND ENZYMATIC ESTERIFICATION METHOD FOR THE PREPARATION OF C-10 ACYLOXY-BEARING

[75] Inventors: Ronald L. Hanson, Morris Plains; Ramesh N. Patel, Bridgewater; Laszlo J. Szarka, East Brunswick, all of N.J.

[73] Assignee: Bristol-Myers Squibb Company, Princeton, N.J.

[21] Appl. No.: 77,980

[22] Filed: Jun. 15, 1993

[51] Int. Cl.$^6$ .............................. C12P 17/02; C12P 17/00
[52] U.S. Cl. ..................... 435/123; 435/117; 435/195; 435/252.1; 435/253.2
[58] Field of Search ................................. 435/123, 117, 435/195, 292.1, 253.2

[56] References Cited

U.S. PATENT DOCUMENTS

| | | |
|---|---|---|
| 4,017,362 | 4/1977 | Miura et al. . |
| 4,582,639 | 4/1986 | Matson et al. . |
| 4,857,653 | 8/1989 | Colin et al. . |
| 4,924,011 | 5/1990 | Denis et al. . |
| 4,924,012 | 5/1990 | Colin et al. . |
| 4,985,060 | 1/1991 | Higa . |

FOREIGN PATENT DOCUMENTS

| | | |
|---|---|---|
| 0253739 | 1/1988 | European Pat. Off. . |
| 0336840 | 10/1989 | European Pat. Off. . |
| 0336841 | 10/1989 | European Pat. Off. . |
| WO93/18018 | 9/1993 | WIPO . |
| WO93/21338 | 10/1993 | WIPO . |

OTHER PUBLICATIONS

A. L. Lehninger, Biochemistry, 2nd Editon, Worth Pub. Inc., 1975, p. 256.
H. Prauser, Bergy's Manual of Systematic Bacteriology, "Genus Nocardioides Prauser 1976,61$^{AL}$", vol. 4, 1989, pp. 2371–2375, S. T. Williams editor, Williams and Wilkins publ.
W. Boland, et al., Synthesis, "Esterolytic and Lipolytic Enzymes in Organic Synthesis", Dec., 1991, pp. 1049–1072.
E. Santaniello, et al., Chem. Rev., "The Biocatalytic Approach to the Preparation of Enantiomerically Pure Chiral Building Blocks", 1992, vol. 92, pp.1071, 1094–1095.

I. Ringel et al., The Journal of Pharmacology and Experimental Therapeutics, "Taxol is Converted to 7–Epitaxol, a Biologically Active Isomer, in Cell Culture Medium", vol. 242, No. 2, pp. 692–698 (1987).

B. Monsarrat, et al., Drug Metabolism and Disposition, "Taxol Metabolism, Isolation and Identification of Three Major Metabolites of Taxol in Rat Bile", vol. 18, No. 6, pp. 895–901 (1990).

D. Kingston, Pharmac. Ther., "The Chemistry of Taxol", vol. 52, pp. 1–34, 1991.

G. Pedrocchi–Fantoni et al., J. Chem. Soc. Perkin Trans. 1, "Regio–and Chemo–selective Properties of Lipase from Candida cylindracea," 1992, pp. 1029–1033.

V. S. Parmar, et al., Tetrahedron, "Regioselective Deacylation of Polyacetoxy Aryl–methyl Ketones by Lipases in Organic Solvents", vol. 48, No. 31, pp. 6495–6498, 1992.

M. Berger et al. Biotechnology Letters, "Regioselectivity of Lipases in Organic Solvents", vol. 13, No. 5, pp. 333–338 (1991).

R. Hanson et al., "Biotransformation of Taxus extracts with site–specific enzymes for hydrolysis of taxanes at C–10 and C–13", Biological Abstracts, xol. 97, 1994, Philadelphia, PA, US; abstract No. 206030, *abstract* 207th National Meeting of the American Chemical Society, San Diego, Mar. 13–17, 1994, Abstracts of Papers America Chemical Society 207 (1–2) 1994 Conference.

D. Cazzulino, et al., "Fermentation and Recovery of an Enzyme Used for Hydrolysis of Taxanes", Biological Abstracts, xol. 97, 1994, Philadelphia, PA, US; abstract No. 205977, *abstract* 207th National Meeting of the American Chemical Society, San Diego, Mar. 13–17, 1994. Abstracts of Papers American Chemical Society 207 (1–2) 1994 Conference.

*Primary Examiner*—Herbert J. Lilling
*Attorney, Agent, or Firm*—Suzanne E. Babajko

[57] ABSTRACT

An enzymatic hydrolysis method, wherein one or more C-10 acyloxy-bearing taxanes are contacted with an enzyme or microorganism capable of hydrolyzing said acyloxy groups to hydroxyl groups. Also provided is an enzymatic esterification method, wherein one or more C-10 hydroxyl-bearing taxanes are contacted with an acylating agent and an enzyme or microorganism capable of esterifying said hydroxyl groups to form acyloxy groups.

24 Claims, No Drawings

ENZYMATIC HYDROLYSIS METHOD FOR THE PREPARATION OF C-10 HYDROXYL-BEARING TAXANES AND ENZYMATIC ESTERIFICATION METHOD FOR THE PREPARATION OF C-10 ACYLOXY-BEARING

FIELD OF THE INVENTION

The present invention relates to an enzymatic hydrolysis method for the preparation of C-10 hydroxyl-bearing taxanes, and an enzymatic esterification method for the preparation of C-10 acyloxy-bearing taxanes, which compounds may be used, for example, as intermediates in the preparation of pharmacologically active taxanes such as taxol and taxol analogues.

BACKGROUND OF THE INVENTION

Taxanes are diterpene compounds which find utility in the pharmaceutical field. For example, taxol, a taxane having the structure:

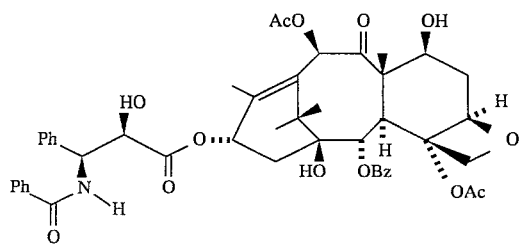

where Ph is phenyl, Ac is acetyl and Bz is benzoyl, has been found to be an effective anticancer agent.

Naturally occurring taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for synthetic, including semi-synthetic routes for the preparation of naturally occurring taxanes such as taxol, as well as for the preparation of analogues thereof.

Due to the complexity of the taxane ring structure, a taxane containing desired substituents on the ring system may more readily be prepared by the use of a starting material already having the basic taxane ring structure. Thus, for example, a compound having the taxane ring structure with a hydroxyl group at C-13, and containing a desired substituent at C-10, may be coupled with an intermediate compound to form a pharmacologically active taxane having an acyloxy sidechain at C-13 such as taxol or an analogue thereof.

SUMMARY OF THE INVENTION

The present invention provides methods for obtaining taxanes with desired substituents at C-10. In particular, the present invention provides methods for the preparation of C-10 hydroxyl-bearing, and C-10 acyloxy-bearing taxane compounds, which compounds find utility as starting materials in the preparation of taxanes such as taxol and analogues thereof.

In one embodiment, the present invention provides a method for the preparation of at least one taxane containing a hydroxyl group directly bonded at C-10, comprising the steps of contacting at least one taxane containing an acyloxy group directly bonded at C-10 with an enzyme or microorganism capable of catalyzing the hydrolysis of said acyloxy group to a hydroxyl group, and effecting said hydrolysis.

In another embodiment, the present invention provides a method for the preparation of at least one taxane containing an acyloxy group directly bonded at C-10, comprising the steps of contacting at least one taxane containing a hydroxyl group directly bonded at C-10 with an acylating agent and an enzyme or microorganism capable of catalyzing the esterification of said hydroxyl group to an acyloxy group, and effecting said esterification.

DETAILED DESCRIPTION OF THE INVENTION

The present invention provides efficient methods for the preparation of C-10 hydroxyl-bearing taxanes from C-10 acyloxy-bearing taxanes, and for the preparation of C-10 acyloxy-bearing taxanes from C-10 hydroxyl-bearing taxanes. A single taxane may be hydrolyzed, or a mixture of different taxanes may be sequentially or simultaneously hydrolyzed, according to the present invention; likewise, a single taxane may be esterified, or a mixture of different taxanes may be sequentially or simultaneously esterified, according to the present invention.

The present invention is described further as follows.

Hydrolysis

In a preferred embodiment, the present invention provides a method for the preparation of at least one C-10 hydroxyl-bearing taxane of the following formula I:

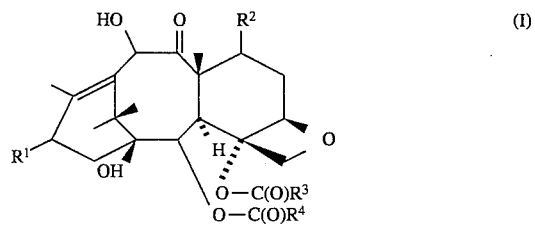

where $R^1$ is hydroxyl or acyloxy, especially where $R^1$ has the structure of formula III described below;

$R^2$ is hydrogen, hydroxyl, fluoro, $R^5$—O—, xylosyl, $R^6$—C(O)—O— or $R^6$—O—C(O)—O—;

$R^3$ and $R^4$ are independently hydrogen, alkyl, alkenyl, alkynyl, cycloalkyl, cycloalkenyl, aryl, or heterocyclo;

$R^5$ is a hydroxyl protecting group; and $R^6$ is hydrogen, alkyl, alkenyl, alkynyl, cycloalkyl, cycloalkenyl, aryl or heterocyclo, or salts thereof, comprising the steps of contacting at least one C-10 acyloxy-bearing taxane of the following formula II:

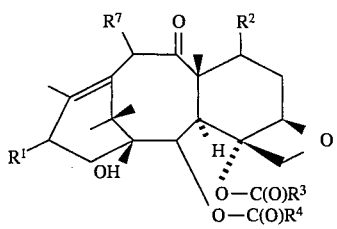

(II)

where $R^1$, $R^2$, $R^3$ and $R^4$ are as defined above; and $R^7$ is acyloxy, or salts thereof, with an enzyme or microorganism capable of catalyzing the hydrolysis of said $R^7$ acyloxy group to a hydroxyl group, and effecting said hydrolysis.

All stereoconfigurations of the unspecified chiral centers of the compounds of the formulae I and II are contemplated in the hydrolysis method of the present invention, either alone (that is, substantially free of other stereoisomers) or in admixture with other stereoisomeric forms.

In another preferred embodiment, the present invention provides a method for the preparation of at least one first taxane, having a desired C-10 acyloxy group, from at least one second taxane, having an undesired acyloxy C-10 group, by enzymatic hydrolysis of the latter to provide at least one C-10 hydroxyl-containing analogue by the method described herein, followed by coupling of the desired acyl group thereto to provide the former. In this embodiment, the present invention provides, for example, a method for the preparation of a desired taxane, having a particular C-10 acyloxy group, from a starting mixture of taxanes containing different acyloxy C-10 groups, which starting mixture may or may not include the desired taxane, by simultaneous or sequential hydrolysis of the different C-10 groups to provide one or more taxanes having a hydroxyl group at C-10, followed by coupling of the desired acyl group thereto. This preferred method is particularly useful where a mixture of taxanes having different C-10 acyloxy groups is obtained, such as by extraction of plant materials yielding taxol in admixture with other naturally-produced taxanes, and where a particular taxane such as taxol is ultimately desired. Coupling of the acyl group may be done by nonenzymatic methods for the formation of acyl groups. For example, C-7 protected 10-desacetylbaccatin III (e.g., protected at C-7 by triethylsilyl formed by contacting 10-desacetylbaccatin III with triethylsilylchloride and imidazole in dimethylformamide) may be acylated at C-10 by contact with lithium hexamethyldisilazide in tetrahydrofuran with lithium chloride/acetyl chloride at low temperatures, e.g. –60° to 70° C. Alternatively, coupling of the acyl group may be done by the enzymatic esterification method described herein.

In the method of the present invention, the stereoconfiguration of the C-10 acyloxy group of the starting taxane is preferably retained in the C-10 hydroxyl group-containing product.

Esterification

In another preferred embodiment, the present invention provides a method for the preparation of at least one C-10 acyloxy-bearing taxane of the following formula II:

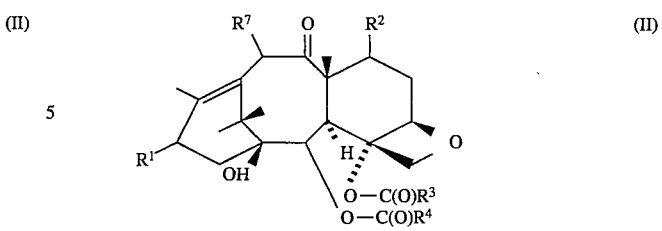

(II)

where $R^1$ is hydroxyl or acyloxy, especially where $R^1$ has the structure of formula III described below;

$R^2$ is hydrogen, hydroxyl, fluoro, $R^5$—O—, xylosyl, $R^6$—C(O)—O— or $R^6$—O—C(O)—O—;

$R^3$ and $R^4$ are independently hydrogen, alkyl, alkenyl, alkynyl, cycloalkyl, cycloalkenyl, aryl, or heterocyclo;

$R^5$ is a hydroxyl protecting group;

$R^6$ is hydrogen, alkyl, alkenyl, alkynyl, cycloalkyl, cycloalkenyl, aryl or heterocyclo; and $R^7$ is acyloxy, or salts thereof, comprising the steps of contacting at least one C-10 hydroxyl-bearing taxane of the following formula I:

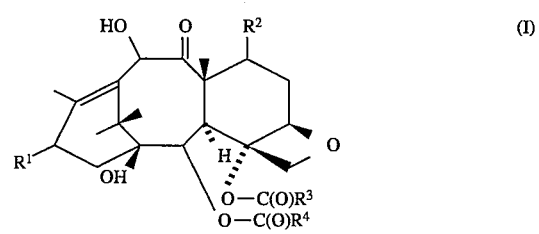

(I)

where $R^1$, $R^2$, $R^3$ and $R^4$ are as defined above, or salts thereof, with an acylating agent and an enzyme or microorganism capable of catalyzing the esterification of the C-10 hydroxyl group to form said $R^7$ acyloxy group, and effecting said esterification.

All stereoconfigurations of the unspecified chiral centers of the compounds of the formulae I and II are contemplated in the esterification method of the present invention, either alone (that is, substantially free of other stereoisomers) or in admixture with other stereoisomeric forms.

Any acylating agent effecting the esterification of the present invention may be employed. Preferred acylating agents are those of the following formula IV:

$$R^{11}\text{—C(O)—L} \qquad \text{(IV)}$$

where $R^{11}$ is alkyl, alkenyl, alkynyl, aryl, cycloalkyl, cycloalkenyl or heterocyclo; and L is a leaving group which may be displaced to form an ester group.

Preferred $R^{11}$ groups for the formula IV are alkyl groups such as C1-6 alkyl groups, especially methyl. Exemplary L groups include halogen atoms, hydroxyl, alkoxy, or alkenyloxy groups. Preferred L groups are alkenyloxy groups, most preferably $C_{1-6}$ alkenyloxy groups such as $CH_2$=CH—O— and $CH_2$=$C(CH_3)$—O—. Isopropenyl acetate and vinyl acetate are particularly preferred acylating agents.

In the method of the present invention, the stereoconfiguration of the C-10 hydroxyl group of the starting taxane is preferably retained in the C-10 acyloxy group-containing product.

Definitions

The terms "enzymatic process" or "enzymatic method", as used herein, denote a process or method of the present invention employing an enzyme or microorganism. The term "hydrolysis", as used herein, denotes the formation of a hydroxyl group from an acyloxy group, and may be achieved, for example, by contact with water and/or a suitable organic alcohol according to the method of the present invention. The term "esterification", as used herein, denotes the formation of an acyloxy group from a hydroxyl group. The term "acylating agent", as used herein, denotes a compound capable of effecting the aforementioned esterification by providing an acyl group. Use of "an enzyme or microorganism" in the present method includes use of two or more, as well as a single, enzyme or microorganism.

The terms "alkyl" or "alk", as used herein alone or as part of another group, denote optionally substituted, straight and branched chain saturated hydrocarbon groups, preferably having 1 to 12 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl", as used herein alone or as part of another group, denote such optionally substituted groups as described above for alkyl having 1 to 4 carbon atoms in the normal chain.

The terms "alkoxy" or "alkylthio", as used herein alone or as part of another group, denote an alkyl group as described above bonded through an oxygen linkage (—O—) or a sulfur linkage (—S—), respectively. The term "alkyloxycarbonyl", as used herein alone or as part of another group, denotes an alkoxy group bonded through a carbonyl group. The term "alkylcarbonyloxy", as used herein alone or as part of another group, denotes an alkyl group bonded through a carbonyl group which is, in turn, bonded through an oxygen linkage. The terms "monoalkylamino" or "dialkylamino", as used herein alone or as part of another group, denote an amino group substituted by one or two alkyl groups as described above, respectively.

The term "alkenyl", as used herein alone or as part of another group, denotes such optionally substituted groups as described above for alkyl, further containing at least one carbon to carbon double bond. Exemplary substituents include one or more alkyl groups as described above, and/or one or more groups described above as alkyl substituents. The term "alkenyloxy", as used herein alone or as part of another group, denotes an alkenyl group as described above bonded through an oxygen linkage (—O—).

The term "alkynyl", as used herein alone or as part of another group, denotes such optionally substituted groups as described above for alkyl, further containing at least one carbon to carbon triple bond. Exemplary substituents include one or more alkyl groups as described above, and/or one or more groups described above as alkyl substituents. The term "alkynyloxy", as used herein alone or as part of another group, denotes an alkynyl group as described above bonded through an oxygen linkage (—O—).

The term "cycloalkyl", as used herein alone or as part of another group, denotes optionally substituted, saturated carbocyclic ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents. The term "cycloalkyloxy", as used herein alone or as part of another group, denotes a cycloalkyl group as described above bonded through an oxygen linkage (—O—).

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents. The term "cycloalkenyloxy", as used herein alone or as part of another group, denotes a cycloalkenyl group as described above bonded through an oxygen linkage (—O—).

The terms "ar" or "aryl", as used herein alone or as part of another group, denote optionally substituted, carbocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents. The term "aryloxy", as used herein alone or as part of another group, denotes an aryl group as described above bonded through an oxygen linkage (—O—).

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one or more alkyl groups as described above and/or one or more groups described above as alkyl substituents. The term "heterocyclooxy", as used herein alone or as part of another group, denotes a heterocyclo group as described above bonded through an oxygen linkage (—O—).

The terms "halogen" or "halo", as used herein alone or as part of another group, denote chlorine, bromine, fluorine, and iodine.

The term "taxane", as used herein, denotes compounds containing a taxane moiety as described following. The term "taxane moiety", as used herein, denotes moieties containing the core structure (with numbering of ring system positions used herein shown):

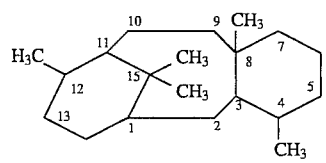

which core structure may be substituted and which may contain ethylenic unsaturation in the ring system thereof.

Such moieties having an oxetane ring fused at the 4- and 5-positions, such as is found in taxol, are preferred.

The term "hydroxy (or hydroxyl) protecting group", as used herein, denotes any group capable of protecting a free hydroxyl group which, subsequent to the reaction for which it is employed, may be removed without disturbing the remainder of the molecule. Such groups, and the synthesis thereof, may be found in "Protective Groups in Organic Synthesis" by T. W. Greene, John Wiley and Sons, 1981, or Fieser & Fieser.

The term "salt", as used herein, includes acidic and/or basic salts formed with inorganic and/or organic acids and bases.

The term "acyl", as used herein alone or as part of another group, denotes the moiety formed by removal of the hydroxyl group from the group —COOH of an organic carboxylic acid. The term "acyloxy", as used herein alone or as part of another group, denotes an acyl group as described above bonded through an oxygen linkage (—O—).

Starting Materials

The C-10 acyloxy-bearing, and C-10 hydroxy-bearing taxanes, employed as starting materials for the present invention may be any such compounds capable of undergoing the enzymatic hydrolysis or esterification methods, respectively, of the present invention. The starting materials may be synthetically formed taxanes, or preferably, LD59 naturally formed taxanes such as cephalomannine, 7-xylosyltaxol, taxol, baccatin III, 10-desacetylbaccatin III, or taxol C (an analogue of taxol wherein the benzoyl group of the C-13 taxol sidechain is replaced by an n-pentanoyl group), alone or in admixture with each other. The "naturally formed" taxane starting materials are preferably obtained by plant cell culture of, and/or extraction from, taxane-producing plant tissues, particularly tissues from, or derived from, plants of the Taxus genus such as *Taxus baccata, Taxus cuspidata, Taxus brevifolia, Taxus wallichiana, Taxus media, Taxus hicksii*, especially *Taxus x. media hicksii*. Exemplary plant tissues include the needles, bark and whole seedling.

For preferred methods of obtaining the C-10 hydroxy- and acyloxy-bearing taxane starting materials of the present methods see Rao, *Pharmaceutical Research*, 10, 521–524 (1993); Kingston, *Pharmac. Ther.*, 52, 1–34 (1991); or the Examples herein.

Enzymes and Microorganisms

The enzyme or microorganism employed in the present invention may be any enzyme or microorganism capable of catalyzing the enzymatic hydrolysis or esterification methods described herein. The enyzmatic or microbial materials, regardless of origin or purity, may be employed in the free state or immobilized on a support such as by physical adsorption or entrapment.

Exemplary microorganisms include those within the following genera: Nocardioides, Nocardia, Rhodococcus, Micropolyspora, Saccharopolyspora, Pseudonocardia, Oerskovia, Promicromonospora, and Intrasporangium. Particularly preferred microorganisms are those species within the genus Nocardioides, such as *Nocardioides albus, Nocardioides flavus, Nocardioides fulvus, Nocardioides luteus, Nocardioides simplex*, and *Nocardioides thermolilacinus*, especially *Nocardioides albus* ATCC 55424 (SC 13910) and ATCC 55425 (SC 13911) and *Nocardioides luteus* ATCC 55426 (SC 13912). The term "ATCC" as used herein refers to the accession number of the American Type Culture Collection, 12301 Parklawn Drive, Rockville, Md. 20852, the depository for the organism referred to. The above microorganisms ATCC 55424, 55425 and 55426 were deposited on May 12, 1993. The term "SC" denotes the designation given to the microorganism as part of the Squibb culture collection.

The biologically pure microorganisms *Nocardioides albus* ATCC 55424 (SC 13910), *Nocardioides albus* ATCC 55425 (SC 13911), and *Nocardioides luteus* ATCC 55426 (SC 13912) are novel microorganisms. It should be understood that mutants of these organims are also contemplated by the present invention, for use in the hydrolysis or esterification methods described herein, such as those modified by the use of chemical, physical (for example, X-rays) or biological means (for example, by molecular biology techniques).

*Nocardioides albus* ATCC 55424 (SC 13910) and ATCC 55425 (SC 13911) may be cultivated on Medium A 94 (corn steep liquor (35 grams), Cerelose (20 grams), $(NH_4)_2SO_4$ Reagent Grade (5 grams), $CaCO_3$ (3.5 grams), soy bean oil (5 ml) and distilled water (1 liter)). These organisms were isolated from soil (from a sample from New Brunswick, N.J.), and are gram positive, non-motile organisms exhibiting aerobic growth on a variety of media. On solid YS medium (0.2% yeast extract, 1% starch), the mycelium is whitish to light cream colored. Growth is associated with production of a dark diffusible pigment in both solid and liquid media. Microscopically, growth in liquid culture is characterized by mycelial aggregates consisting of abundantly branching hyphae.

*Nocardioides luteus* ATCC 55426 (SC 13912) may be cultivated on Medium A 94 (corn steep liquor (35 grams), Cerelose (20 grams), $(NH_4)_2SO_4$ Reagent Grade (5 grams), $CaCO_3$ (3.5 grams), soy bean oil (5 ml) and distilled water (1 liter)). This organism was isolated from soil (from a sample from New Brunswick, N.J.), and is a gram positive, non-motile organism exhibiting aerobic growth on a variety of media. On solid YS medium (0.2% yeast extract, 1% starch), the mycelium is dark cream colored. Microscopically, growth in liquid culture is characterized by mycelial aggregates consisting of abundantly branching hyphae.

The above organisms *Nocardioides albus* ATCC 55424 (SC 13910) and ATCC 55425 (SC 13911), and *Nocardioides luteus* ATCC 55426 (SC 13912), were identified as strains of *Nocardioides albus* and *Nocardioides luteus*, respectively, in accordance with the description given in *Bergey's Manual of Systematic Bacteriology*, Volume 2 (Ed. P. H. A. Sneath) (1986).

Exemplary enzymes for use in the present hydrolysis or esterification methods are hydrolases, particularly esterases, proteases or lipases. Preferred enzymes include those derived from microorganisms, particularly those microorganisms described above. Enzymes may be isolated, for example, by extraction and purification methods, such as by use of hydrophobic interaction chromatography, gel filtration, followed by an anion exchange column. The present invention further provides the enzymes capable of the present hydrolysis or esterification methods which may be isolated from *Nocardioides albus* ATCC 55424 (SC 13910) and ATCC 55425 (SC 13911), and *Nocardioides luteus* ATCC 55426 (SC 13912), for example, by the above techniques.

Where microorganisms are employed, the cells may be used in the form of intact wet cells or dried cells such as lyophilized, spray-dried or heat-dried cells, or in the form of treated cell material such as ruptured cells or cell extracts.

The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic hydrolysis or esterification methods of the present invention may be carried out subsequent to the fermentation of the microorganism (two-stage fermentation and hydrolysis or esterification), or concurrently therewith, that is, in the latter case, by in situ fermentation and hydrolysis or esterification (single-stage fermentation and hydrolysis or esterification).

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources may include N-Z amine A, corn steep liquor, soy bean meal, beef extracts, yeast extracts, molasses, baker's yeast, tryprone, nutrisoy, peptone, yeastamin, amino acids such as sodium glutamate and the like, sodium nitrate, ammonium sulfate and the like.

Trace elements may include magnesium, manganese, calcium, cobalt, nickel, iron, sodium and potassium salts. Phosphates may also be added in trace, or preferably, greater than trace amounts.

The medium employed may include more than one carbon or nitrogen source or other nutrient.

Preferred media for growth include aqueous media, particularly those described in the Examples herein.

The agitation and aeration of the reaction mixture affects the amount of oxygen available during the hydrolysis or esterification process when conducted, for example, in shake-flask cultures or fermentor tanks during growth of microorganisms. The agitation range from 100 to 250 RPM is preferred; aeration of about 1 to 10 volumes of air per volume of media per minute is preferred.

For growth of the microorganisms and/or hydrolysis or esterification according to the method of the present invention, the pH of the medium is preferably from about 6 to about 8.5, and the temperature is preferably from about 24° C. to about 37° C. Hydrolysis or esterification may, for example, be carried out in vitro over time periods such as 1 to 48 hours, or preferably until the yield of desired product is maximized. It is preferred to conduct the hydrolysis of the present invention at a pH of from 6 to 8, particularly under non-basic conditions.

It is also preferred to employ an aqueous liquid as the hydrolysis reaction medium, although an organic liquid, or a miscible or immiscible (biphasic) organic/aqueous liquid mixture, may also be employed. It is preferred to employ an organic solvent or biphasic organic/aqueous reaction medium for esterification, although other media may be employed. It is preferred to employ 0.025 to 2.5 weight % of the C-10 hydroxy- or acyloxy-bearing taxane starting material(s) based on the combined weight of starting material(s) and esterification or hydrolysis reaction medium. In the esterification method of the present invention, preferred molar ratios of acylating agent to C-10 hydroxyl-bearing taxane are from about 1:1 to about 1000:1.

The amount of enzyme or microorganism employed relative to the starting material is selected to allow catalysis of the enzymatic hydrolysis or esterification of the present invention. It is preferred to obtain yields in excess of 90% (% C-10 hydrolyzed product obtained based on the starting acyloxy-bearing taxane) or in excess of 50% (% C-10 acylated product obtained based on the starting hydroxyl-bearing taxane) when employing the hydrolysis or esterification methods of the present invention, respectively. Hydrolysis or esterification may be obtained selectively at C-10 of the starting taxane. That is, product(s) the greater portion (such as solely) of which are hydrolyzed or esterified at C-10 only may be obtained without hydrolysis or esterification at other positions.

Separation

The C-10 acyloxy- or hydroxyl-bearing products of the processes of the present invention, and coupled products such as those described below, may be isolated and purified, for example, by methods such as extraction, distillation, crystallization, and column chromatography.

Utility

Taxanes are diterpene compounds containing a taxane moiety as described above. Of particular interest are taxanes containing a taxane moiety in which the 11,12-positions are bonded through an ethylenic linkage, and in which the 13-position contains a sidechain, which taxanes are exemplified by taxol. Pharmacologically active taxanes such as taxol may be used as antitumor agents to treat patients suffering from cancers such as breast, ovarian, colon or lung cancers, melanoma and leukemia.

The compounds obtained by the hydrolysis or esterification methods of the present invention are particularly useful as intermediates in the preparation of the aforementioned pharmacologically active taxanes by allowing preparation of compounds having a desired substituent at C-10. Thus, for example, where the compounds prepared by the methods of the present invention also bear a hydroxyl group at C-13, such compounds may be coupled with C-13 acyloxy sidechain-forming intermediate compounds, such as β-lactams, to obtain C-13 acyloxy sidechain-bearing taxanes such as taxol or analogues thereof. In this regard, modification at C-13 according to U.S. patent application Ser. No. 08/077, 979, entitled "Enzymatic Hydrolysis Method for the Preparation of C-13 Hydroxy-bearing Taxanes, and Use Thereof in the Preparation of C-13 Acyloxy-bearing Taxanes", by Hanson et al., filed concurrently herewith (Attorney Docket No. LD58), incorporated herein by reference, may be conducted prior to, during, or after the methods of the present invention are employed. The acyloxy- or hydroxyl-bearing compounds prepared according to the methods of the present invention may optionally be modified prior to use in such C-13 acyloxy sidechain coupling. For example, one or more hydroxyl groups at positions other than C-13 may be protected prior to coupling and, thereafter, deprotected.

The C-10 acyloxy- and hydroxyl-bearing taxanes obtained by the hydrolysis and esterification methods of the present invention, optionally modified as above, may, for example, be used in the preparation of C-13 acyloxy sidechain-bearing taxanes such as those recited, and prepared by the methods described in, European Patent Publication No. 400,971, U.S. Pat. Nos. 4,876,399, 4,857,653, 4,814,470, 4,924,012, 4,924,011, and Kingston, *Pharm. Ther.*, Vol. 52, 1–34 (1991), especially U.S. patent application Ser. No. 07/995,443, filed Dec. 23, 1992 by Poss et al. (Attorney Docket No. LD60) and U.S. patent application Ser. No. 08/033,598, filed Mar. 19, 1993 by Thottathil et al. (Attorney Docket No. LD57), all incorporated herein by reference.

Preferred Compounds

It is preferred to employ taxanes of the formula II or salts thereof in the hydrolysis method of the present invention, whereby enzymatic hydrolysis provides the corresponding compounds of the formula I or salts thereof. It is likewise preferred to employ taxanes of the formula I or salts thereof in the esterification method of the present invention, whereby enzymatic esterification provides the corresponding compounds of the formula II or salts thereof.

In formulae I and II, $R^7$ is preferably $R^{11}$—C(O)—O—, especially where $R^{11}$ is alkyl such as methyl; $R^2$ is preferably hydroxyl or xylosyl; $R^3$ is preferably alkyl such as methyl; $R^4$ is preferably aryl such as phenyl; and $R^1$ is preferably hydroxyl or a group of the following formula III:

where $R^8$ and $R^9$ are independently alkyl, alkoxy, alkenyl, alkenyloxy, alkynyl, alkynyloxy, cycloalkyl, cycloalkyloxy, cycloalkenyl, cycloalkenyloxy, aryl, aryloxy, heterocyclo or heterocyclooxy; and $R^{10}$ is hydrogen or a hydroxyl protecting group.

Exemplary taxanes of the formulae I and II are cephalomannine, 10-desacetyltaxol, 7-xylosyltaxol, taxol-C, 7-xylosyl-10-desacetyltaxol, taxol, baccatin III, 10-desacetylbaccatin III, 7-xylosylbaccatin III, and 7-xylosyl-10-desacetylbaccatin III. Enzymatic hydrolysis of baccatin III to form 10-desacetylbaccatin III (e.g., with the formation of acetic acid), for example, employing hydrolase, is a preferred embodiment of the present invention. This reaction may be reversed via the enzymatic esterification method of the present invention.

Taxol is preferably ultimately prepared by the methods described herein.

Salts or solvates such as hydrates of reactants or products may be employed or prepared as appropriate in any of the methods of the present invention.

The present invention is further described by the following examples which are illustrative only, and are in no way intended to limit the scope of the instant claims.

Example 1

10-Deacetylation of Baccatin III

*Nocardioides luteus* ATCC 55426 (SC 13912) isolated from soil was grown for three days at 28° C., 150 rpm in a 50 ml Erlenmeyer flask containing 10 ml medium. The medium contained per liter distilled water: 10 g Bacto tryprone, 5 g Bacto yeast extract, 6 ml tributyrin, and 0.06 ml Tween 80 at a final pH of 6.8±0.2. Cells were harvested by centrifugation, washed with 10 ml 50 mM potassium phosphate buffer pH 7, and resuspended in 2 ml of this buffer. 0.5 mg baccatin III in 20 μl methanol was added to the cell suspension and the suspension was mixed for 20 hours at ambient temperature (about 23° C.) with a Fisher Roto-Rack. The suspension was extracted with methylene chloride, and the extract was evaporated, redissolved and assayed by HPLC Method 2 described following. The sample contained 0.257 mg/ml 10-desacetylbaccatin III (100% conversion) and only a trace of baccatin III. Washed cells of the strain ATCC 55426 grown on three other media also carried out this transformation.

Example 2

10-Deacetylation of Baccatin III

*Nocardioides luteus* ATCC 55426 (SC 13912) grown in 20 ml medium containing per liter distilled water: 10 g Bacto tryprone, 5 g Bacto yeast extract and 0.06 ml Tween 80 at a pH of 6.8±0.2 was used to inoculate 1 L of the same medium in a 4 L Erlenmeyer flask. The flask was shaken for three days at 28° C., then cells were harvested by centrifugation. The cell pellet was washed with 600 ml 50 mM potassium phosphate buffer pH 7 and centrifuged again to give 36.6 g wet cells. The cells were frozen at −72° C., lyophilized to 2.5 g in 2 days, ground with a mortar and pestle and stored at 2° C. 1.98 ml 50 mM potassium phosphate buffer pH 7, 50 mg dried cells, and 0.5 mg baccatin III in 20 μl methanol were mixed with a Roto-Rack at ambient temperature for the times indicated on Table 1 following. Reactions were stopped by addition of 2 ml methanol. Precipitate was removed with a microfuge, and samples were assayed by HPLC Method 1 described following. The results obtained are shown in Table 1.

TABLE 1

| Time (Min) | 10-desacetyl-baccatin III mg/ml | Baccatin III mg/ml | Conversion (%) |
|---|---|---|---|
| 0 | 0.007 | 0.252 | — |
| 30 | 0.051 | 0.143 | 22 |
| 60 | 0.106 | 0.106 | 46 |
| 120 | 0.204 | 0.034 | 88 |

Example 3

10-Deacetylation Of Taxol

A partially purified extract from *Nocardioides luceus* ATCC 55426 (SC 13912) (purified by anion exchange chromatography on Whatman DE52) contained 34 milliunits/ml enzyme. (1 milliunit is the amount of enzyme able to hydrolyze 1 nmole baccatin III to 10-desacetylbaccatin III per minute at 28° C. in 50 mM potassium phosphate buffer pH 7 containing 0.25 mg/ml baccatin III and 1% methanol.) 2 ml containing 50 mM potassium phosphate buffer pH 7, 0.5 mg taxol, 1% methanol, and 34 milliunits enzyme was incubated on a Fisher RotoRack for 3.5 hours at 28° C. The reaction was stopped by extraction with 4 ml methylene chloride. The extract was dried, redissolved in methanol and assayed by HPLC Method 3 described following. The sample contained 0.075 mg taxol and 0.186 mg/ml 10-desacetyltaxol (78% conversion).

Alternative Purification of *Nocardioides luteus* ATCC 55426 (SC 13912)

*Nocardioides luteus* ATCC 55426 was grown in a fermentor on a medium containing 1% tryprone and 0.5% yeast extract. All purification steps were carried out at 4° C. in 50 mM phosphate buffer pH 7.2. The cells were suspended at 10% w/v in buffer and passed through a micro-fluidizer twice at 10,000 psi for lysis. The cell lysate was then clarified by centrifugation at 24,000×g for 15 min. Ammonium sulfate was added to 60% saturation and the resulting precipitate was suspended in buffer containing 1M ammonium sulfate and applied to a hydrophobic interaction chromatography (HIC-ether (Toya-pearl)) column (5.5×2.6 cm) at a flow rate of 2 ml/min. The enzyme activity was eluted with buffer. The active fractions were then loaded on a Pharmacia Sephacryl S-200 gel 5 filtration column (2.6×84 cm) at 0.5 ml/min. The active fractions from the column were loaded on an anion exchange (BioRad-Q2) column (2 ml column, flow rate 2 ml/min) and the activity was eluted with a salt gradient of 0–0.8M NaCl in 42 ml. The active fractions were pooled and applied to a Sephacryl S-200 column as described above. The molecular weight of the enzyme was estimated to be 40,000±10,000 on gels containing sodium dodecyl sulfate. The results obtained at various steps of the above method were as follows:

| Step* | Volume ml | Protein mg | Activity mu | Specific Activity mu/mg | Recovery % |
|---|---|---|---|---|---|
| Cell extract | 100 | 450 | 2050 | 4.5 | — |
| Amm. Sulfate | 70 | 196 | 2830 | 14.4 | 138 |
| HIC (ether) | 7 | 24 | 953 | 39.9 | 46.5 |
| Sephacryl S-200 | 7 | 0.7 | 190 | 271 | 9.3 |
| BioRad-Q2 | 3 | 0.09 | 51 | 567 | 2.5 |
| Sephacryl S-200 | 8 | 0.03 | 26 | 867 | 1.3 |

*Purification of C-10-deacetylase: 1 milliunit enzyme (mu) catalyzes the conversion of 1 nmole/min of baccatin-III to 10-deacetylbaccatin-III at 25° C. in 50 mM potassium phosphate buffer, pH 7, containing 0.25 mg/ml baccatin-III and 1% methanol. Protein was determined with BioRad Protein Assay Reagent.

Example 4

Acetylation of 10-Desacetylbaccatin III to Baccatin III

*Nocardioides luteus* ATCC 55426 (SC 13912) cells in 50 mM potassium phosphate buffer pH 7.2 (10% weight/volume) were disrupted with a microfluidizer and the 10-deacetylase enzyme was adsorbed from the extract on Whatman DEAE cellulose DE52 anion exchanger by stirring for 3 hours (10 g extract protein per liter DE52). The DE52 was collected by filtration, washed with buffer and lyophilized to give 0.091 milliunits enzyme per mg solid. 0.2 ml 1M potassium phosphate buffer pH 8, 100 mg immobilized enzyme (i.e., immobilized on the DE52 resin), 1.8 ml water, 2 mg 10-desacetylbaccatin III and 0.5 ml vinyl acetate were vigorously stirred with a magnetic bar for 14.5 hours at room temperature. The reaction mixture was extracted with methylene chloride. The extract was dried and redissolved in methanol for analysis by HPLC Method 1 described following. The sample contained 0.688 mg/ml 10-desacetylbaccatin III and 0.203 mg/ml baccatin III (19% conversion).

HPLC Methods

Method 1
Column: Hewlett Packard hypersil 5 micron ODS C18 200×4.6 mm Mobile phase: 55% methanol, 45% water Flow rate: 1 ml/min Column temperature: ambient Detection wavelength: 235 nm Method 2
Column: Phase Separations Inc. (Norwalk, Conn.) microbore spherisorb phenyl 150×2.0 mm, 3 micron Mobile phase: Solvent A:15 mM $KH_2PO_4$, adjusted to pH 4 with trifluoroacetic acid. Solvent B: acetonitrile

| Time/Minute | Solvent A (%) | Solvent B (%) |
|---|---|---|
| 0 | 75 | 25 |
| 20 | 55 | 45 |
| 23 | 40 | 60 |
| 24 | 25 | 75 |
| 28 | 75 | 25 |

Column temperature: 35° C. Detection wavelength: 230 nm.

Method 3
Column: Hewlett Packard hypersil 5 micron ODS C18 200×4.6 mm Mobile phase: 60% methanol, 40% water Flow Rate: 1 ml/min Column temperature: ambient Detection wavelength: 235 nm Example 5

Hydrolysis of Seedling Extract

An ethanol extract of *Taxus hicksii* seedlings was concentrated 10- to 15-fold with nanofilters. 0.5 ml extract, 0.5 ml 1M potassium phosphate buffer pH 7, 54 milliunits partially purified enzyme from *Nocardioides albus* ATCC 55425 (SC 13911) (purified by anion exchange chromatography and ammonium sulfate precipitation) and 4 ml water were incubated at 28° C. for 48 hours on a Fisher Roto Rack. (An enzyme from ATCC 55425 may be employed for the hydrolysis at C-13 as described in U.S. patent application Ser. No. 08/077,979, entitled "Enzymatic Hydrolysis Method for the Preparation of C-13 Hydroxyl-Bearing Taxanes, and Use Thereof in the Preparation of C-13 Acyloxy-Bearing Taxanes", filed concurrently herewith by Hanson et al.). A second tube contained the same mixture and also 14 milliunits enzyme from *Nocardioides luteus* ATCC 55426 (SC 13912) immobilized on 500 mg DE52 as described in Example 4. After 23 hours incubation at 28° C., a second portion of 14 milliunits enzyme from ATCC 55426 on DE52 was added along with 4 ml water, and incubation was continued for 22 hours. A control sample received no enzymes. Samples were extracted with methylene chloride, and the evaporated extracts were dissolved in methanol for analysis by HPLC Method 2 described above. The results obtained are shown in Table 2 following.

The results show that, after treatment with the C-13 deacylase from SC 13911, there was depletion of taxol, cephalomannine, 7-xylosyl-10-deacetyltaxol and 10-deacetyltaxol, while the amount of baccatin III and 10-deacetylbaccatin III increased. The molar ratios of 10-deacetylbaccatin III to initial taxol was increased from 117% to 436%. When the seedling extract was treated with both the C-13 deacylase from SC 13911 and the C-10 deacylase from SC 13912, baccatin III was converted to 10-deacetylbaccatin III and the concentration of 10-deacetylbaccatin III was increased by 6-fold compared to the initial value. Thus, treatment of a mixture of taxanes with the C-13 deacylase and C-10 deacylase gave 10-deacetylbaccatin III as the principle product.

TABLE 2

| | Hydrolysis of Seedling Extract | | | | | |
|---|---|---|---|---|---|---|
| Enzyme from | 10-desacet-ylbaccatin III mg/ml | baccatin III mg/ml | 7-xylosyl-10-desacet-yltaxol mg/ml | cephalo-mannine mg/ml | taxol mg/ml | 10-DAT mg/ml |
| None | 0.167 | 0.142 | 0.246 | 0.243 | 0.401 | 0.201 |
| SC13911 | 0.400 | 0.771 | 0.027 | 0.000 | 0.000 | 0.014 |
| 11 + 12+ | 1.025 | 0.000 | 0.000 | 0.000 | 0.000 | 0.000 |
| | taxol C mg/ml | D + B/T* | | | | |
| None | trace | 116.8 | | | | |
| SC13911 | 0.000 | 436.3 | | | | |
| 11 + 12 | 0.000 | 400.8 | | | | |

10-DAT is 10-desacetyltaxol
+SC13911 and SC13912
*D + B/T is the molar % yield of (10-deacetylbaccatin III and baccatin III) divided by (initial taxol)

What is claimed is:

1. A method for the preparation of at least one taxane containing a hydroxyl group directly bonded at C-10, comprising the steps of contacting at least one taxane containing an acyloxy group directly bonded at C-10 with a microorganism belonging to the genus Nocardiodes, or an enzyme derived therefrom, which is capable of catalyzing the hydrolysis of said acyloxy group to a hydroxyl group, and effecting said hydrolysis.

2. The method of claim 1, wherein at least one C-10 hydroxyl-bearing taxane of the following formula I is prepared:

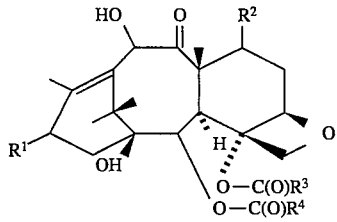

where $R^1$ is hydroxyl or acyloxy;

$R^2$ is hydrogen, hydroxyl, fluoro, $R^5$—O—, xylosyl, $R^6$—C(O)—O— or $R^6$—O—C(O)—O—;

$R^3$ and $R^4$ are independently hydrogen, alkyl, alkenyl, alkynyl, cycloalkyl, cycloalkenyl, aryl, or heterocyclo;

$R^5$ is a hydroxyl protecting group; and $R^6$ is hydrogen, alkyl, alkenyl, alkynyl, cycloalkyl, cycloalkenyl, aryl or heterocyclo, or a salt thereof, by contacting at least one C-10 acyloxy-bearing taxane of the following formula II:

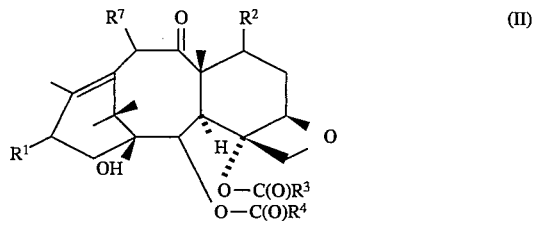

where $R^1$, $R^2$, $R^3$ and $R^4$ are as defined above; and $R^7$ is acyloxy, or a salt thereof, with an enzyme or microorganism capable of catalyzing the hydrolysis of said $R^7$ acyloxy group to a hydroxyl group.

3. The method of claim 2, wherein said taxane of the formula II is baccatin III, and wherein said taxane of the formula I is 10-desacetylbaccatin III.

4. The method of claim 1, wherein the acyloxy-bearing taxane starting material employed in said hydrolysis method comprises a mixture of acyloxy-bearing taxanes.

5. The method of claim 4, wherein said mixture of taxanes is obtained by plant cell culture of, and/or extraction from, plant tissue, wherein said plant is a member of the Taxus genus.

6. The method of claim 1, wherein said microorganism is selected from the group consisting of Nocardioides albus, Nocardioides flavus, Nocardioides fulvus, Nocardioides luteus, Nocardioides simplex, and Nocardioides thermolilacinus.

7. The method of claim 6, wherein said microorganism is selected from the group consisting of Nocardioides albus ATCC 55424 (SC 13910), Nocardioides albus ATCC 55425 (SC 13911), and Nocardioides luteus ATCC 55426 (SC 13912).

8. The method of claim 1, wherein said enzyme is derived from a microorganism selected from the group consisting of Nocardioides albus, Nocardioides flavus, Nocardioides fulvus, Nocardioides luteus, Nocardioides simplex, and Nocardioides thermolilacinus.

9. The method of claim 8, wherein said enzyme is derived from a microorganism selected from the group consisting of *Nocardioides albus* ATCC 55424 (SC 13910), *Nocardioides albus* ATCC 55425 (SC 13911), and *Nocardioides luteus* ATCC 55426 (SC 13912 ).

10. The method of claim 1, wherein the taxane product obtained is employed in the preparation of a taxane bearing an acyloxy group at C-13.

11. A method for the preparation of at least one taxane containing an acyloxy group directly bonded at C-10, comprising the steps of contacting at least one taxane containing a hydroxyl group directly bonded at C-10 with an acylating agent and a microorganism belonging to the genus Nocardioides, or an enzyme derived therefrom, which is capable of catalyzing the esterification of said hydroxyl group to an acyloxy group, and effecting said esterification.

12. The method of claim 11, wherein at least one C-10 acyloxy-bearing taxane of the following formula II is prepared:

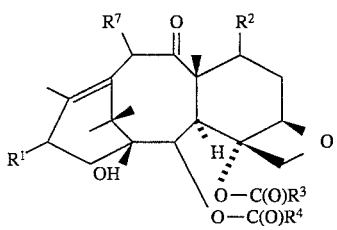

where $R^1$ is hydroxyl or acyloxy;

$R^2$ is hydrogen, hydroxyl, fluoro, $R^5$—O—, xylosyl, $R^6$—C(O)—O— or $R^6$—O—C(O)—O—;

$R^3$ and $R^4$ are independently hydrogen, alkyl, alkenyl, alkynyl, cycloalkyl, cycloalkenyl, aryl, or heterocyclo;

$R^5$ is a hydroxyl protecting group;

$R^6$ is hydrogen, alkyl, alkenyl, alkynyl, cycloalkyl, cycloalkenyl, aryl or heterocyclo; and $R^7$ is acyloxy, or a salt thereof, by contacting at least one C-10 hydroxyl-bearing taxane of the following formula I:

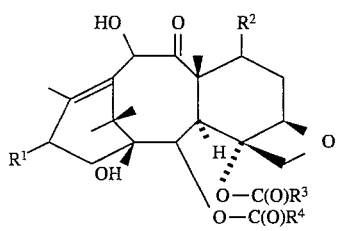

where $R^1$, $R^2$, $R^3$ and $R^4$ are as defined above, or a salt thereof, with an acylating agent and an enzyme or microorganism capable of catalyzing the esterification of the C-10 hydroxyl group to form said $R^7$ acyloxy group.

13. The method of claim 12, wherein said taxane of the formula II is baccatin III, and wherein said taxane of the formula I is 10-desacetylbaccatin III.

14. The method of claim 11, wherein the hydroxy-bearing taxane starting material employed in said esterification method comprises a mixture of hydroxy-bearing taxanes.

15. The method of claim 14, wherein said mixture of taxanes is obtained by plant cell culture of, and/or extraction from, plant tissue, wherein said plant is a member of the Taxus genus.

16. The method of claim 11, wherein said microorganism is selected from the group consisting of *Nocardioides albus, Nocardioides flavus, Nocardioides fulvus, Nocardioides luceus, Nocardioides simplex,* and *Nocardioides thermolilacinus.*

17. The method of claim 16, wherein said microorganism is selected from the group consisting of *Nocardioides albus* ATCC 55424 (SC 13910), *Nocardioides albus* ATCC 55425 (SC 13911), and *Nocardioides luteus* ATCC 55426 (SC 13912).

18. The method of claim 11, wherein said enzyme is derived from a microorganism selected from the group consisting of *Nocardioides albus, Nocardioides flavus, Nocardioides fulvus, Nocardioides luteus, Nocardioides simplex,* and *Nocardioides thermolilacinus.*

19. The method of claim 18, wherein said enzyme is derived from a microorganism selected from the group consisting of *Nocardioides albus* ATCC 55424 (SC 13910), *Nocardioides albus* ATCC 55425 (SC 13911), and *Nocardioides luteus* ATCC 55426 (SC 13912).

20. The method of claim 11, wherein said acylating agent is a compound of the following formula IV:

$$R^{11}—C(O)—L \qquad (IV)$$

where $R^{11}$ is alkyl, alkenyl, alkynyl, aryl, cycloalkyl, cycloalkenyl or heterocyclo; and L is a leaving group which may be displaced to form an ester group.

21. The method of claim 20, wherein said acylating agent is vinyl acetate.

22. The method of claim 11, wherein the taxane product obtained is employed in the preparation of a taxane bearing an acyloxy group at C-13.

23. The method of claim 10, wherein taxol is prepared as the taxane bearing an acyloxy group at C-13.

24. The method of claim 22, wherein taxol is prepared as the taxane bearing an acyloxy group at C-13.

* * * * *

UNITED STATES PATENT AND TRADEMARK OFFICE
CERTIFICATE OF CORRECTION

PATENT NO. : 5,523,219

DATED : June 4, 1996

INVENTOR(S) : Ronald L. Hanson, et al.

It is certified that error appears in the above-identified patent and that said Letters Patent is hereby corrected as shown below:

```
On the cover page, in line 6 of the title of this patent,
after "ACYLOXY-BEARING" insert --TAXANES--.
Column 1, line 6, after "ACYLOXY-BEARING" insert --TAXANES--.
Column 18, line 17, "luceus" should read --luteus--.
```

Signed and Sealed this

Sixth Day of August, 1996

*Attest:*

BRUCE LEHMAN

*Attesting Officer*     *Commissioner of Patents and Trademarks*